US008592574B2

(12) United States Patent
Song et al.

(10) Patent No.: US 8,592,574 B2
(45) Date of Patent: Nov. 26, 2013

(54) BETA-GLUCAN-BASED SCAFFOLD FOR BIOLOGICAL TISSUE ENGINEERING USING RADIATION FUSION TECHNOLOGY, AND PRODUCTION METHOD THEREFOR

(75) Inventors: Sung Ki Song, Bucheon-si (KR); Yong Man Jang, Wonju-si (KR); In Ho Jeon, Ansan-si (KR); Sang Jin Ko, Incheon (KR); Jeong Rhan Jeon, Seoul (KR); Gie Taek Chun, Chuncheon-si (KR); Youn Mook Lim, Jeongeup-si (KR); Hui Jeong Kwon, Jeonju-si (KR)

(73) Assignee: Quegen Biotech Co., Ltd., Siheung-Si, Gyeonggi-Do (KR)

( * ) Notice: Subject to any disclaimer, the term of this patent is extended or adjusted under 35 U.S.C. 154(b) by 95 days.

(21) Appl. No.: 13/144,851

(22) PCT Filed: Jan. 22, 2010

(86) PCT No.: PCT/KR2010/000430
§ 371 (c)(1),
(2), (4) Date: Jul. 27, 2011

(87) PCT Pub. No.: WO2010/085119
PCT Pub. Date: Jul. 29, 2010

(65) Prior Publication Data
US 2011/0275795 A1    Nov. 10, 2011

(30) Foreign Application Priority Data

Jan. 22, 2009   (KR) ........................ 10-2009-0005343
Jan. 22, 2010   (KR) ........................ 10-2010-0005912

(51) Int. Cl.
*C07H 3/06*      (2006.01)
(52) U.S. Cl.
USPC .................................................. 536/123.12
(58) Field of Classification Search
USPC .................................................... 536/123.12
See application file for complete search history.

(56) References Cited

U.S. PATENT DOCUMENTS

| 5,688,775 | A | 11/1997 | Renn et al. |
|---|---|---|---|
| 6,723,429 | B2 | 4/2004 | Bengs et al. |
| 2003/0144127 | A1 | 7/2003 | Berggren et al. |
| 2004/0209360 | A1 | 10/2004 | Keith et al. |
| 2007/0009579 | A1 * | 1/2007 | Sato .............................. 424/443 |

FOREIGN PATENT DOCUMENTS

| CN | 1944495 A | 11/2007 |
|---|---|---|
| JP | 2001-046487 | 2/2001 |
| KR | 1020070102589 | 10/2007 |
| KR | 1020090009513 A | 1/2009 |
| WO | WO 2004/098503 A2 | 11/2004 |

OTHER PUBLICATIONS

Wasser S.P. Medicinal mushrooms as a source of antitumor and immunomodulating polysaccharides. Appl Microbiol Biotechnol 60:258-274, Sep. 2002.*
Michalek, M. et al, Journal of Leukocyte Biology. vol. 64, Sep. 1998, pp. 337-344.
Lee SB, Jeon HW, Lee YW. Lee YM, Song KW, Park MH, Nam YS, Ahn HC; "Bio-Artlficial Skin Composed of Gelatin and (1→3), (1→6)-Beta-Glucan"; Biomaterials, 2003 Jun:24(14).

* cited by examiner

*Primary Examiner* — Wu-Cheng Winston Shen
*Assistant Examiner* — Yih-Horng Shiao
(74) *Attorney, Agent, or Firm* — Lucas & Mercanti, LLP

(57) ABSTRACT

The present invention relates to a beta-glucan-based scaffold for biological tissue engineering using radiation fusion technology, and to a production method therefor. According to the production method of the present invention for beta-glucan-based scaffold, radiation fusion tissue engineering, a beta-glucan-aqueous solution is cast and is then irradiated in a crosslinking reaction in such a way as to form a gel or solid scaffold, thereby facilitating cell attachment and making it easy to create a biomimetic environment coinductive to the growth and differentiation of stem cells. Consequently, the beta-glucan-based scaffold according to the present invention can be usefully employed as a filler for tissue regeneration, cell culturing and plastic surgery, as a filler for voids in biological tissue, as a scaffold for reconstructive and corrective plastic surgery, and for cell transplantation and drug delivery.

7 Claims, 5 Drawing Sheets

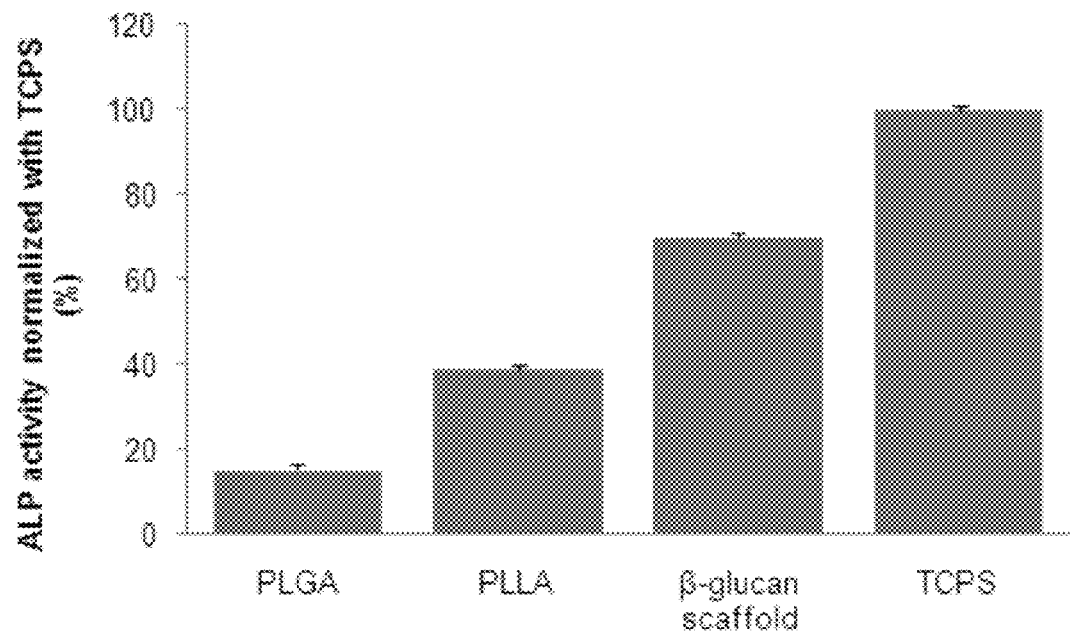

BETA-GLUCAN-BASED SCAFFOLD FOR BIOLOGICAL TISSUE ENGINEERING USING RADIATION FUSION TECHNOLOGY, AND PRODUCTION METHOD THEREFOR

CROSS-REFERENCE TO RELATED APPLICATIONS

This application is a 371 of PCT/KR2010/000430 filed Jan. 22, 2010, which claims the benefit of Korean Patent Application No. 10-2009-0005343 filed Jan. 22, 2009 and Korean Patent Application No. 10-2010-0005912 filed Jan. 22, 2010, the contents of each of which are incorporated herein by reference.

TECHNICAL FIELD

The present invention relates to a beta-glucan-based scaffold for tissue engineering, and a method for the production thereof, using radiation fusion technology.

BACKGROUND ART

Tissue engineering is a technology adapted for culturing cells on scaffolds to form cell-scaffold complexes and applying them to fabricate tissues or organs for clinical use. According to the principle of tissue engineering, cells are isolated from a tissue of interest taken from a patient and cultured in a scaffold to form a cell-scaffold complex which is then implanted into the patient. Most definitions of tissue engineering cover a broad range of applications to the repair or replace of almost any human organ including, inter alia, artificial skin, artificial bones, artificial cartilage, artificial corneas, artificial vessels, artificial muscles, etc. To optimize the regeneration of tissues or organs, the provision of a scaffold similar to a bodily tissue may be the first priority. For use in tissue engineering, scaffolds fundamentally allow cells to adhere thereto and act as frames capable of supporting three-dimensional tissue formation. Also, scaffolds are required to be non-toxic and biocompatible as not to elicit blood coagulation and inflammatory reactions. That is, scaffolds for tissue engineering may be preferably biocompatible polymers which are friendly to adjacent tissues in the body and bioadhesive without suffering from graft rejection. Biocompatible polymers are largely divided into natural polymers and synthetic polymers or into biodegradable polymers and non-biodegradable polymers. Examples of the natural polymers include protein-based polymers such as collagen, albumin, and amino acids; and polysaccharides and derivatives thereof, such as cellulose, agarose, alginate, heparin, hyaluronic acid, chitosan, etc.

Damaged thermal tissue, especially severely burnt skin is typically replaced with one of 1) autografts, obtained from the same individual to which they will be reimplanted, 2) allografts, which come from the body of a donor of the same species and 3) xenografts, which are isolated from individuals of another species. Autografts, although ideal, are problematic in that when a large area of the skin is injured, there are limited autografts available. Further, the acquisition of a thermal autograft causes another injury to the skin. As for allografts, they are used as a support that aids the migration and proliferation of cells around the injury rather than for purposes of eternal engraftment. A typical allograft is cadaver tissue or skin. Although immune responses may be avoided, there remains the problem of the shortage of allograft donors. To overcome such problems, active research has been directed toward the development of highly biocompatible natural or synthetic polymers suitable as scaffolds for the reconstruction of artificial skin.

To date, various crosslinking techniques have been extensively applied to natural polymers to produce biomaterials. The production of biomaterials by reacting chemical reagents, however, may be expensive because the reactions may have to be conducted under certain conditions in the presence of catalysts, and furthermore, the catalysts may be toxic. Further, there is always the possibility of the presence of impurities in the final product, which may, even should the chemical reagents be used in a very small amount, cause unanticipated side effects.

As a solution to this problem, radiation crosslinking for developing biomaterials has been studied. In radiation crosslinking, the absence of harmful chemicals including crosslinking agents, initiators and so on eradicates a post-radiation process of removing, for example, residual crosslinking agents or initiators. Also, radiation crosslinking can simultaneously guarantee both sterilization and crosslinking. In addition, this process enjoys the advantage of the crosslinking requiring no additional heat, making it possible to crosslink even materials which are in a refrigerated state, and readily controlling physical properties of the materials only with radiation doses, without changing compositions.

Beta-glucan ($\beta$-1,6-branched-$\beta$-1,3-glucan) is almost free of calories and has a generally recognized as safe statusin the United States of America following its approval by the FDA in 1983. It exhibits a variety of physiological activities including anticancer activity, wound healing, immunopotentiation, promotion of collagen biosynthesis, cell regeneration, high water retention, etc. As extensive research has proven the safety thereof for years, beta-glucan derived from Basidomycetes finds application in various fields including medicines, cosmetics, health foods, animal food additives, etc. In spite of its biocompatibility and various physiological activities, beta-glucan has not yet been developed or studied as a scaffold for tissue engineering thus far.

Beta-glucan with high biocompatibility and a variety of physiological activities is considered to exhibit no toxicity in the body. When radiation fusion technology is applied thereto, beta-glucan can be developed into a scaffold for tissue engineering which allows cells to readily adhere thereto and provides a biomimetic environment effective for the growth and differentiation of stem cells. There is therefore a need for the development of beta-glucan-based scaffolds in tissue engineering.

DISCLOSURE

Technical Problem

Leading to the present invention, intensive and thorough research into the development of beta-glucan-based scaffolds for tissue engineering, conducted by the present inventors, resulted in the finding that when human mesenchymal stem cells was grown and differentiated into osteocytes thereon, the scaffold in a gel or solid form, obtained by crosslinking an aqueous beta-glucan-based scaffold cast onto a petri-dish or a flat plate with radiation, allowed the cells to have a total DNA content and ALP activity at a level similar to that on TCPS, thus providing higher differentiation potency, compared to conventional nano-fiber scaffolds.

Technical Solution

In order to accomplish the above object, the present invention provides a radiation-applied, beta-glucan-based scaffold and a method for producing the same.

DESCRIPTION OF DRAWINGS

FIG. 5 is a graph showing ALP activity after human mesenchymal stem cells were grown for two days and differentiated for 14 days on the beta-glucan-based scaffold of the present invention, PLGA (poly lactic-co-glycolic acid), PLLA (poly lactic acid), and TCPS.

BEST MODE

Figure 1:
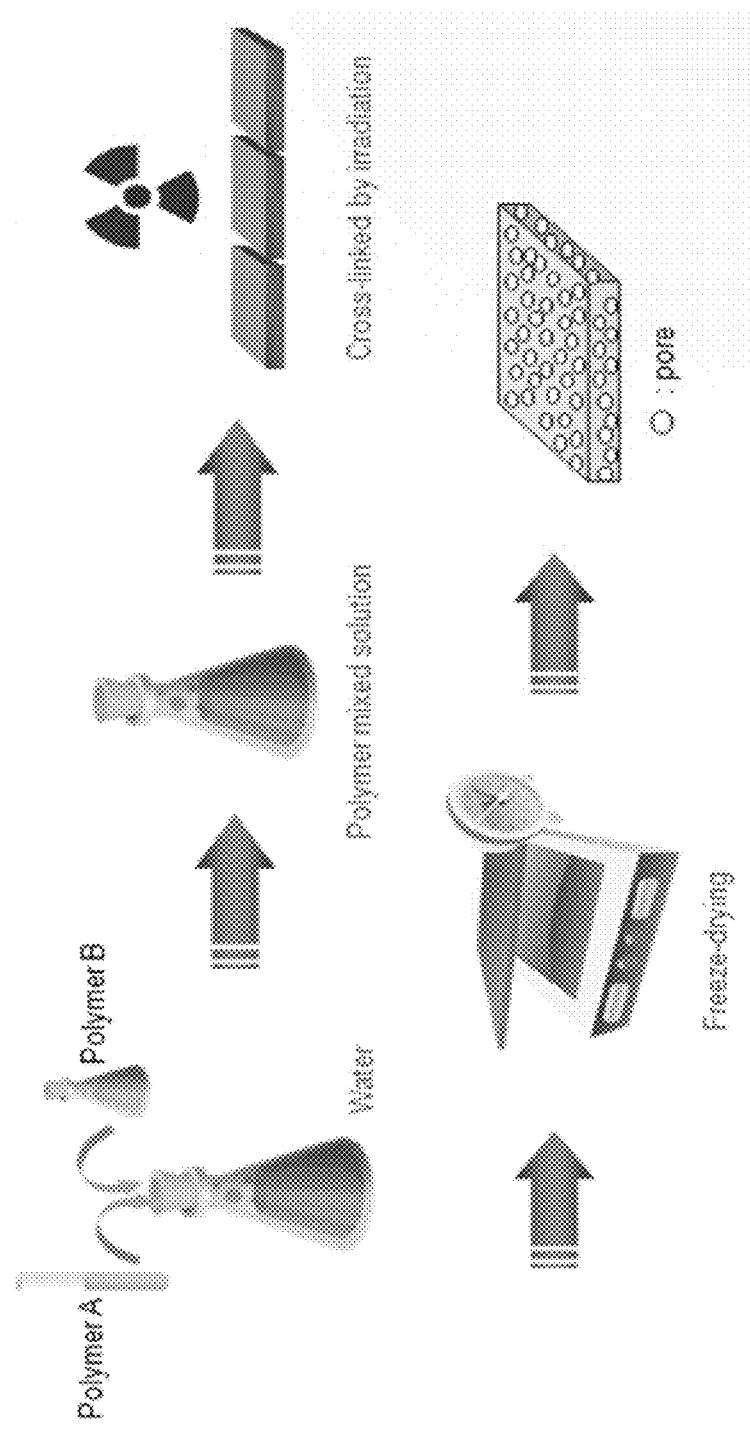
FIG. 1 is a schematic diagram illustrating the process of producing a beta-glucan-based scaffold for tissue engineering, using radiation fusion technology.

In accordance with an aspect thereof, the present invention provides a method for producing a beta-glucan-based scaffold for tissue engineering, comprising:

1) dissolving a powder of beta-glucan at 30~100° C. for 30~200 min in distilled water to form a 0.1~50 wt % aqueous beta-glucan solution;
2) casting the aqueous beta-glucan solution onto a petri-dish or a flat plate; and
3) crosslinking the beta-glucan cast with radiation at a dose of 5~50 kGy to produce the scaffold in a gel or solid form.

Optionally, the method for producing a beta-glucan-based scaffold in accordance with the present invention may further comprise subjecting the crosslinked beta-glucan cast to rapid refrigeration at −50~−100° C. and immediate thawing to induce pores to form within the scaffold after step 3).

In addition, the present invention provides a beta-glucan-based scaffold for tissue engineering, produced by the method.

A detailed description will be given of the present invention, below.

The method for producing a beta-glucan-based scaffold for tissue engineering, using radiation fusion technology, in accordance with the present invention is characterized by casting an aqueous beta-glucan solution on a petri-dish or a flat plate, irradiating the cast with radiation to conduct a crosslink reaction to produce the scaffold in a gel or solid form.

The beta-glucan useful in the present invention may be preferably selected from the group consisting of *Schizophyllum commune, Ganoderma lucidum, Phellinus linteus, Inonotus Obliquus, Sparassis crispa, Agaricus blazei* Murrill, *Grifola frondosa*, Shiitake mushroom, *Sclerotinia sclertiorum*, yeast, barley, oats and a combination thereof, but are not limited thereto. In the present invention, the beta-glucan extracted from *Schizophyllum commune*, called *schizophyllan*, was used.

In the aqueous beta-glucan solution, beta-glucan is contained in an amount of from 0.1 to 50 wt %, preferably in an amount of from 4 to 15 wt %, and most preferably in an amount of wt %. For example, if the concentration of beta-glucan exceeds 50 wt %, the aqueous solution is too viscous to cast onto the vessel. On the other hand, when the concentration of beta-glucan is below 0.1 wt %, the aqueous solution is too dilute to elicit a crosslink reaction therein.

As for the casting of the aqueous beta-glucan solution, its amount is 5~20 vol % based the total volume of the casting vessel, and preferably 10 vol %. The casting vessel may be preferably petri-dishes or flat plates of various sizes.

The radiation useful in the present invention may be preferably selected from the group consisting of an electron beam, a gamma beam and a UV beam. The radiation is irradiated into the cast beta-glucan solution at a dose of from 5 to 50 kGy and a preferably at a dose of from 15 to 30 kGy to produce a scaffold in a gel or solid form.

Optionally, the crosslinked beta-glucan cast may be rapidly frozen at −50~−100° C. and immediately thawed to induce the formation of pores therein.

On the beta-glucan-based scaffold thus prepared, human mesenchymal stem cells were cultured for 2 days and allowed to differentiate for 14 days. The cells were measured to have a total DNA of about 380 ng per scaffold, with an ALP content of about 0.7 nmole/DNA/30 min. Generally, osteocytes, after differentiation from human mesenchymal stem cells on TCPS, have a total DNA content of about 500 ng per scaffold while the ALP content is on the order of 0.5~0.6 nmole after differentiation on a conventional nano-fiber scaffold. Therefore, the beta-glucan-based scaffold according to the present invention is understood to allow cells to grow normally thereon. Further, the total DNA content similar to that of cells on TCPS demonstrates that the scaffold of the present invention is almost free of cytotoxicity. The scaffold of the present invention also guaranteed higher differentiation potency to the cells than did the conventional nano-fiber scaffold. In addition, as human mesenchymal stem cells were found to have higher ALP activity when grown on the beta-glucan-based scaffold of the present invention than on PLGA or PLLA, conventional biomaterials used for tissue regeneration, the beta-glucan-based scaffold of the present invention can provide a biomimetic environment more effective for the growth and differentiation of stem cells than can the conventional biomaterial PLGA or PLLA.

As described above, the method for producing a beta-glucan-based scaffold for tissue engineering, using radiation fusion technology in accordance with the present invention, in which an aqueous beta-glucan solution is cast and crosslinked by radiation to produce the scaffold in a gel or solid form, can make a great improvement to cell attachment, embodying a biomimetic environment effective for the growth and differentiation of stem cells. Hence, the beta-glucan-based scaffold according to the present invention can be effectively applied for use in tissue regeneration, cell culture, cell implantation and drug delivery.

Mode for Invention

A better understanding of the present invention may be obtained through the following examples which are set forth to illustrate, but are not to be construed as limiting the present invention.

EXAMPLE 1

Preparation of Beta-Glucan-Based Scaffold Using Radiation Fusion Technology

To 100 mL of distilled water was dissolved 80 g of a powder of *Schizophyllum commune*-derived beta-glucan (Schizophyllan) at 90° C. for 1 hour to give an 8 wt % aqueous beta-glucan solution. This 8 wt % beta-glucan solution was cast into a petri-dish (90×15 mm) in an amount of 10% of the volume of the petri-dish. The beta-glucan cast was irradiated with a gamma ray at a dose of 15~30 kGy to cause a crosslinking reaction. The crosslinked beta-glucan cast was rapidly frozen at −80° C. and immediately thawed to induce the formation of pores within the cast, thus affording a scaffold in gel or solid form.

Figure 2:
FIG. 2 shows the beta-glucan-based scaffold for tissue engineering, produced using the process of FIG. 1.

A process by which a beta-glucan-based scaffold for tissue engineering is fabricated is schematically depicted in FIG. 1 while the beta-glucan-based scaffold produced by the process of FIG. 1 is shown in FIG. 2.

EXPERIMENTAL EXAMPLE 1

Assay of the Inventive Beta-Glucan-Based Scaffold for Potency of Differentiating Human Mesenchymal Stem Cell (hMSC) into Osteocytes The degree of differentiation from human mesenchymal stem cells into osteocytes on the beta-glucan-bases scaffold of the present invention was evaluated as follows.

1. Measurement of Total DNA Content after Differentiation of hMSC on Scaffolds

Human mesenchymal stem cells were seeded at a density of $1\times10^5$ cells/scaffold onto the beta-glucan-based scaffold produced in Example 1 and a TCPS (tissue culture polystyrene) scaffold, separately, followed by proliferation in a complete growth medium [LG-DMEM(GIBCO)+1% PS(GIBCO)+10% FBS(GIBCO 16000)] for two days and then differentiation for 14 days. After two washes with PBS, each of the scaffolds was detached, placed in an EP-tube, and stored at −70° C. until analysis. To each of the EP-tubes containing the scaffolds was added 300 μL of RIPA buffer [150 mM NaCl, 1% Triton X-100, 1% sodium deoxycholate, 0.1% SDS, 150 mM Tris(pH 7.2)], and the scaffolds were finely cut with scissors and homogenized on ice. The scaffolds were removed before DNA measurement.

Figure 3:
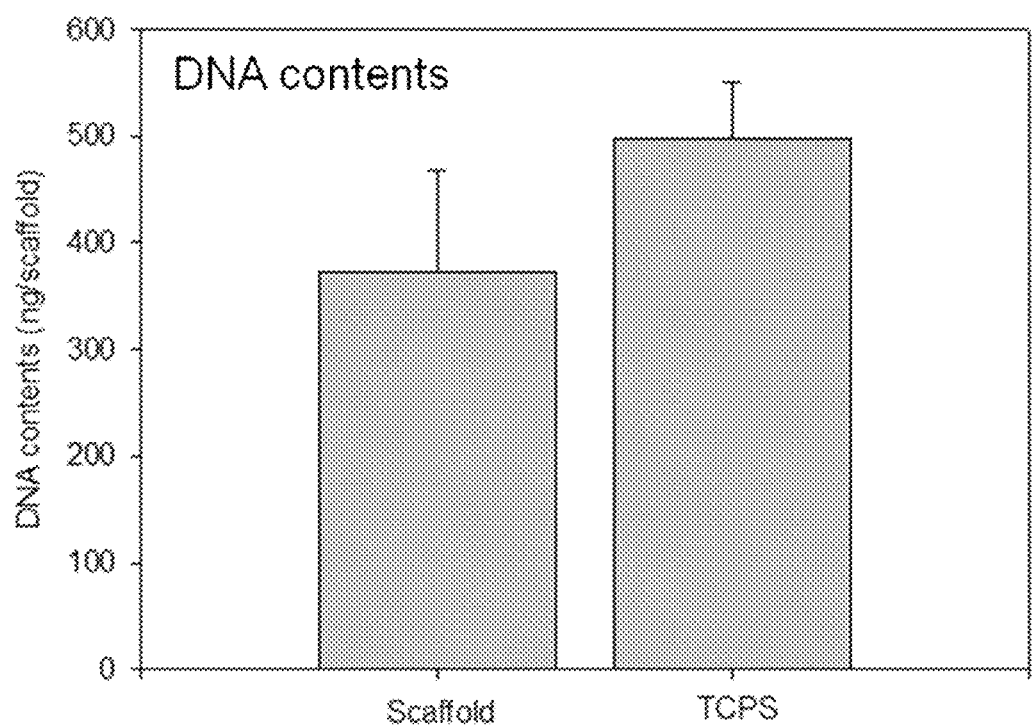
FIG. 3 is a graph showing total DNA content after human mesenchymal stem cells were grown for 2 days and differentiated for 14 days on the beta-glucan-based scaffold of the present invention.

The result is shown in FIG. 3.

As seen in FIG. 3, the human mesenchymal stem cells differentiated into osteocytes with a total DNA content of about 380 ng on the beta-glucan-based scaffold and about 500 ng on TCPS. Thus, the beta-glucan-based scaffold according to the present invention allowed the cells to grow normally and was almost free of cyotoxicity at a level similar to that of TCPS.

2. Measurement of ALP Activity after Differentiation of hMSC on Scaffolds

Human mesenchymal stem cells were seeded at a density of $1\times10^5$ cells/scaffold onto the beta-glucan-based scaffold produced in Example 1, PLGA, PLLA and TCPS, separately, followed by proliferation in a complete growth medium [LG-DMEM(GIBCO)+1% PS(GIBCO)+10% FBS(GIBCO 16000)] for two days and then differentiation for 14 days. After two washes with PBS, each of the scaffolds was detached, placed in an EP-tube, and stored at −70° C. until analysis.

To each of the EP-tubes containing the scaffolds was added 300 μL of RIPA buffer [150 mM NaCl, 1% Triton X-100, 1% sodium deoxycholate, 0.1% SDS, 150 mM Tris(pH 7.2)], and the scaffolds were finely cut with scissors and homogenized on ice. The supernatant (cell lysate) was plated in an amount of 10 μL per well into 96-well plates and mixed with 200 μL of pNPP (alkaline phosphatase yellow) substrate per well before incubation at 37° C. for 30 min. Thereafter, 50 μL of 3N NaOH was added to each well, followed by measuring absorbance at 405 nm. ALP activities were compared, with normalization to the absorbance for TCPS.

Figure 4:
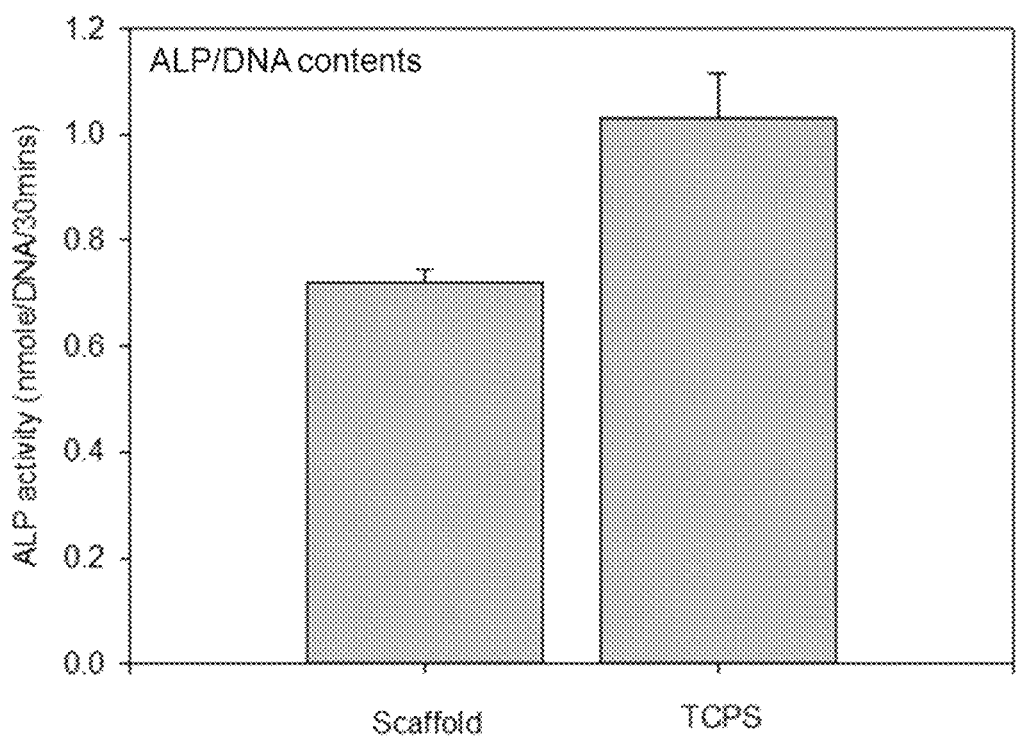
FIG. 4 is a graph showing ALP activity per DNA content of FIG. 3.

ALP activity per DNA content, measured after human mesenchymal stem cells were grown for 2 days and differentiated for 14 days on the beta-glucan-based scaffold of the present invention, is shown in FIG. 4. Measurements of the ALP activity of human mesenchymal stem cells after growth for 2 days and differentiation for 14 days on the beta-glucan-based scaffold of the present invention, PLGA, PLLA and TCPS, are shown in FIG. 5.

As seen in FIG. 4, the ALP level after the differentiation of human mesenchymal stem cells into osteocytes on the beta-glucan-based scaffold of the present invention was on the order of 0.7 nmole/DNA/30 min. Thus, the beta-glucan-based scaffold of the present invention guarantees higher differentiation potency, compared to the conventional nano-fiber scaffolds (up to 0.5~0.6 nmole). Since these results came from the environment of low cell-to-cell contact possibility, higher levels of differentiation potency are anticipated from the scaffold.

After the growth and differentiation of human mesenchymal stem cells on the beta-glucan-based scaffold of the present invention and the conventional biomaterial PLGA or PLLA, as can be seen in FIG. 5, the ALP activity of the cells were on the order of 20~25% and 70%, respectively, of that of cells on TCPS. Therefore, the beta-glucan-based scaffold according to the present invention can provide biomimetic environments more effective in the growth and differentiation of stem cells that can the conventional biomaterials PLGA or PLLA.

INDUSTRIAL APPLICABILITY

As described hitherto, the method for producing a beta-glucan-based scaffold for tissue engineering, using radiation fusion technology in accordance with the present invention, in which an aqueous beta-glucan solution is cast and crosslinked by radiation to produce the scaffold in a gel or solid form, can make a great improvement to cell attachment, embodying a biomimetic environment effective for the growth and differentiation of stem cells. Hence, the beta-glucan-based scaffold according to the present invention can be effectively applied for use in tissue regeneration, cell culture, cell implantation and drug delivery and as fillers for plastic or reconstructive surgery, implants and prosthesis for plastic surgery.

We claim:

1. A method for producing a beta-glucan-based scaffold for tissue engineering, using radiation fusion technology, consisting essentially of:
    a) dissolving a powder of beta-glucan at 30-100° C. for 30-200 min in distilled water to form a 0.1-50wt % aqueous beta-glucan solution;
    b) casting the aqueous beta-glucan solution onto a petri-dish or a flat plate; and
    c) crosslinking the beta-glucan cast in the absence of a chemical crosslinking agent with a radiation at a dose of 5-50 kGy to produce the scaffold in a gel or solid form.

2. The method of claim 1, wherein the beta-glucan is extracted from at least one species selected from the group consisting of *Schizophyllum commune, Ganoderma lucidum, Phellinus linteus, Inonotus Obliquus, Sparassis crispa, Agaricus blazei* Murrill, *Grifola frondosa*, Shiitake mushroom, *Sclerotinia sclertiorum*, yeast, barley and oats.

3. The method of claim 2, wherein the beta-glucan is extracted from *Schizophyllum commune (schizophyllan)*.

4. The method of claim 1, wherein the aqueous beta-glucan solution contains beta-glucan in an amount of 4-15wt % based on a total weight of the solution.

5. The method of claim 1, wherein the aqueous beta-glucan solution is cast in an amount of from 5 to 20 vol % based on a total volume of the petri-dish or plate in step b).

6. The method of claim 1, wherein the radiation of step c) is selected from the group consisting of an electron beam, a gamma beam, and an ultra-violet beam.

7. A method for producing a beta-glucan-based scaffold for tissue engineering, using radiation fusion technology, consisting essentially of:
   a) dissolving a powder of beta-glucan at 30-100° C. for 30-200 min in distilled water to form a 0.1-50 wt % aqueous beta-glucan solution;
   b) casting the aqueous beta-glucan solution onto a petri-dish or a flat plate;
   c) crosslinking the beta-glucan cast in the absence of a chemical crosslinking agent with a radiation at a dose of 5-50 kGy to produce the scaffold in a gel or solid form; and
   d) subjecting the crosslinked beta-glucan to rapid refrigeration from −50 to −100° C. and immediate thawing to induce pore formation within the scaffold.

\* \* \* \* \*